US009476806B2

(12) United States Patent
Hirama et al.

(10) Patent No.: US 9,476,806 B2
(45) Date of Patent: Oct. 25, 2016

(54) SAMPLE PROCESSING SYSTEM

(71) Applicant: HITACHI HIGH-TECHNOLOGIES CORPORATION, Tokyo (JP)

(72) Inventors: Yoshiteru Hirama, Tokyo (JP); Hiroshi Ohga, Tokyo (JP); Tatsuya Fukugaki, Tokyo (JP); Hiroaki Sakai, Tokyo (JP); Kazuma Tamura, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 292 days.

(21) Appl. No.: 14/349,633

(22) PCT Filed: Oct. 1, 2012

(86) PCT No.: PCT/JP2012/075342
§ 371 (c)(1),
(2) Date: Apr. 3, 2014

(87) PCT Pub. No.: WO2013/051495
PCT Pub. Date: Apr. 11, 2013

(65) Prior Publication Data
US 2014/0326082 A1  Nov. 6, 2014

(30) Foreign Application Priority Data

Oct. 7, 2011  (JP) ................................ 2011-223422

(51) Int. Cl.
*G01N 1/00* (2006.01)
*G01N 35/04* (2006.01)
(Continued)

(52) U.S. Cl.
CPC . *G01N 1/00* (2013.01); *B01L 9/06* (2013.01); *G01N 35/04* (2013.01); *B65G 47/244* (2013.01);
(Continued)

(58) Field of Classification Search
CPC ............................................. G01N 2035/0439
USPC ......................................................... 422/65
See application file for complete search history.

(56) References Cited

U.S. PATENT DOCUMENTS 5,008,082 A * 4/1991 Shaw ................. G01N 35/0092
422/547
5,350,564 A * 9/1994 Mazza ................ B01L 3/50855
422/562
(Continued)

FOREIGN PATENT DOCUMENTS

EP     1106542 A1   6/2001
JP    63-271164 A  11/1988
(Continued)

OTHER PUBLICATIONS

International Preliminary Report on Patentability received in International Application No. PCT/JP2012/075342 dated Apr. 17, 2014.
(Continued)

*Primary Examiner* — Hezron E Williams
*Assistant Examiner* — Mark A Shabman
(74) *Attorney, Agent, or Firm* — Mattingly & Malur, PC

(57) ABSTRACT

A sample processing system includes a sample vessel holder including a disk-shaped base section disposed so as to have a central axis extending in a vertical direction and a sample vessel holding section that is formed coaxially with, and above, the base section for holding a sample vessel in an upright posture. A conveyor conveys the sample vessel holder 1 placed thereon; and a holding plate is disposed so as to extend along an outer peripheral portion of a columnar space that has a central axis extending in the vertical direction, and is disposed at a position above a space past which the base section of the sample vessel holder moves along the conveyor and at a position past which at least the sample vessel holding section moves. This enables individual conveyance processing to be performed for each of multiple sample vessels.

8 Claims, 13 Drawing Sheets

(51) Int. Cl.
 *B01L 9/06* (2006.01)
 *B65G 47/53* (2006.01)
 *B65G 47/244* (2006.01)
(52) U.S. Cl.
 CPC ....... *B65G 47/53* (2013.01); *B65G 2201/0261* (2013.01); *G01N 2035/0406* (2013.01); *G01N 2035/047* (2013.01)

(56) References Cited

U.S. PATENT DOCUMENTS

| | | | | |
|---|---|---|---|---|
| 5,380,487 | A * | 1/1995 | Choperena | G01N 35/0092 198/346.2 |
| 5,587,129 | A * | 12/1996 | Kurosaki | G01N 35/00603 422/63 |
| 6,117,683 | A * | 9/2000 | Kodama | G01N 35/00584 422/65 |
| 6,358,472 | B1 * | 3/2002 | DeYoung | G01N 35/0095 422/565 |
| 6,605,213 | B1 * | 8/2003 | Ammann | B01F 9/0001 210/222 |
| 6,919,044 | B1 * | 7/2005 | Shibata | G01N 35/0092 422/63 |
| 6,984,527 | B2 * | 1/2006 | Miller | G01N 35/00 422/562 |
| 7,678,331 | B2 * | 3/2010 | Shanafelter | G01N 35/021 422/65 |
| 8,480,977 | B2 * | 7/2013 | Gunji | B01L 3/0217 422/501 |
| 8,703,492 | B2 * | 4/2014 | Self | G01N 35/04 422/63 |
| 2005/0180884 | A1 | 8/2005 | Itoh | |
| 2008/0038827 | A1 * | 2/2008 | Miller | G01N 35/04 436/43 |
| 2008/0271546 | A1 * | 11/2008 | Miller | G01N 35/0092 73/863.92 |
| 2008/0318306 | A1 | 12/2008 | Le Comte et al. | |
| 2010/0239461 | A1 * | 9/2010 | Itoh | B01L 9/06 422/65 |
| 2010/0282003 | A1 * | 11/2010 | Hamada | G01N 35/00722 73/863.91 |
| 2012/0266698 | A1 * | 10/2012 | Isobe | G01N 35/026 73/863.92 |

FOREIGN PATENT DOCUMENTS

| | | |
|---|---|---|
| JP | 07-239333 A | 9/1995 |
| JP | 3059194 U | 7/1999 |
| JP | 2002-098705 A | 4/2002 |
| JP | 2005-227206 A | 8/2005 |
| JP | 2007-529733 A | 10/2007 |
| JP | 2010-500575 A | 1/2010 |
| JP | 2010-526289 A | 7/2010 |
| JP | 2011-033395 A | 2/2011 |
| JP | 2011-075355 A | 4/2011 |
| WO | 2011028166 A1 | 3/2011 |

OTHER PUBLICATIONS

Extended European Search Report received in corresponding European Application No. 12837932.8 dated Apr. 17, 2015.

* cited by examiner

FIG. 6
FIG. 7
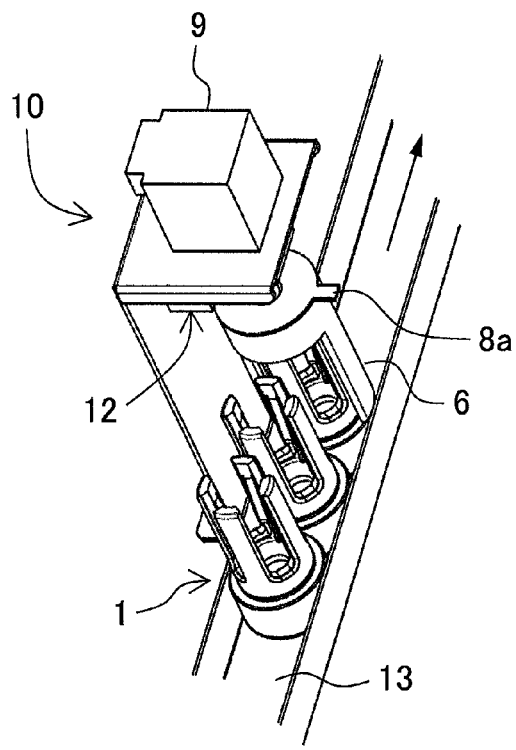
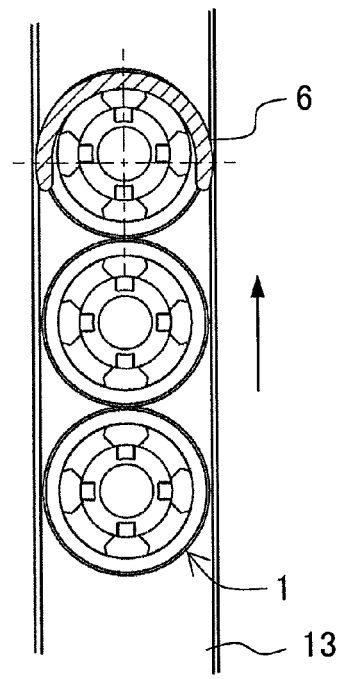

FIG. 8
FIG. 9
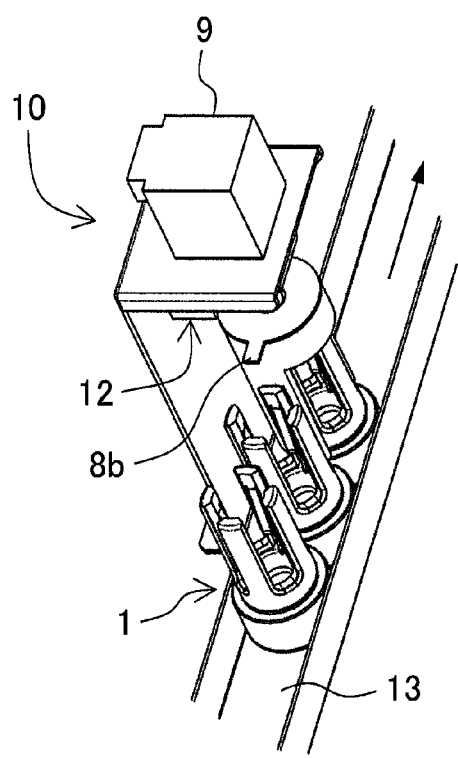
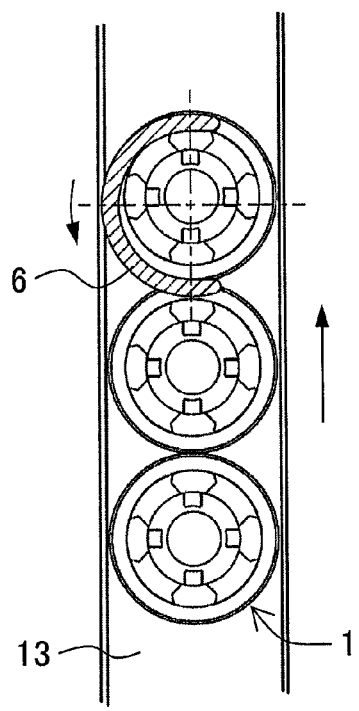

FIG. 16
FIG. 17
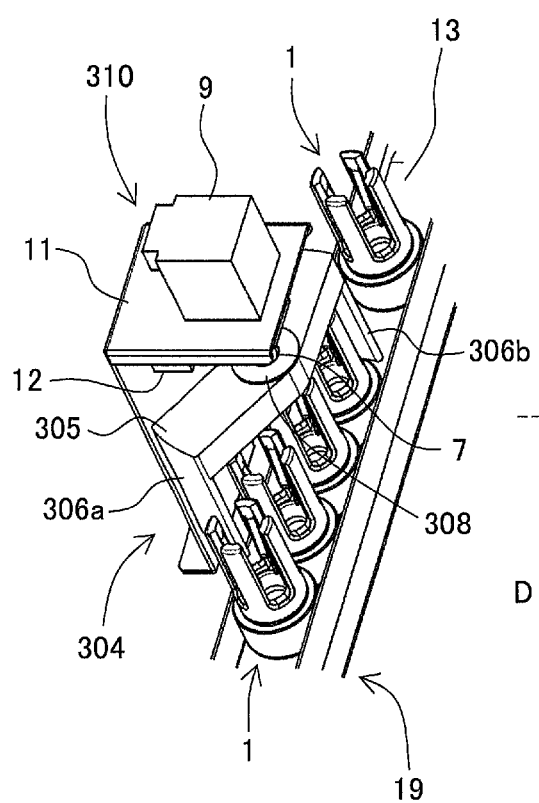
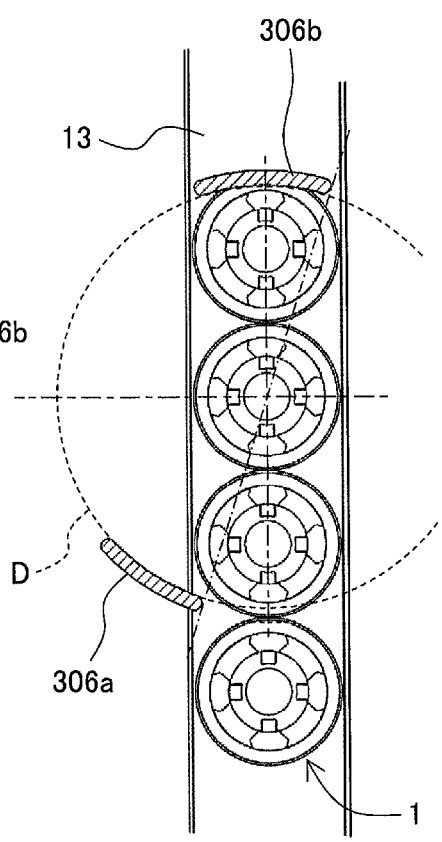

SAMPLE PROCESSING SYSTEM

TECHNICAL FIELD

The present invention relates to a sample processing system that processes a sample such as blood and urine.

BACKGROUND ART

To achieve labor saving and higher speed in testing, sample processing systems that automatically perform preprocessing and conveyance of samples to be loaded in automatic analyzers are used in clinical laboratory settings in which qualitative and quantitative analyses of biological samples such as blood and urine are conducted. Such sample processing systems perform various types of processing for samples stored in, for example, sample vessels and loaded in the systems. Patent document 1 (JP-2011-33395-A), for example, discloses a technique relating to an automatic unplugging apparatus. In the technique, out of a plurality of test tubes held in an upright posture in one row in a test tube rack, the automatic unplugging apparatus simultaneously clamps plug bodies of every other test tube and moves upwardly to thereby remove the plug bodies. The automatic unplugging apparatus then simultaneously clamps plug bodies of the rest of the test tubes and moves upwardly to thereby remove the plug bodies from the rest of the test tubes.

PRIOR ART DOCUMENT

Patent Document

Patent Document 1
JP-2011-33395-A

SUMMARY OF THE INVENTION

Problem to be Solved by the Invention

Conventional sample processing systems perform preprocessing or the like for the samples by conveying a rack that holds a plurality of sample vessels as in the related art. A need, however, exists in recent years for individually conveying a plurality of sample vessels to thereby concurrently perform different analysis processes, thus responding to changes and developments in analysis techniques and further improving processing efficiency.

The present invention has been made in view of the foregoing situation and it is an object of the present invention to provide a sample processing system capable of conveying individually a plurality of sample vessels.

Means for Solving the Problem

To achieve the foregoing object, the present invention provides a sample processing system that comprises: a sample vessel holder including a disk-shaped base section disposed so as to have a central axis extending in a vertical direction and a sample vessel holding section that is formed coaxially with, and above, the base section and has an outside diameter smaller than that of the base section, the sample vessel holding section holding a sample vessel in an upright posture; a conveying path that conveys the sample vessel holder placed thereon; and a holder holding mechanism including a holding plate disposed so as to extend along an outer peripheral portion of a columnar space that has a central axis extending in the vertical direction, and disposed at a position above a space past which the base section of the sample vessel holder moves along the conveying path and at a position past which at least the sample vessel holding section moves. The holder holding mechanism controls through a circumferential movement of the holding plate a conveyance state of the sample vessel holder conveyed by the conveying path.

Effect of the Invention

The present invention enables individual conveyance processing to be performed for each of multiple sample vessels.

BRIEF DESCRIPTION OF THE DRAWINGS

FIG. 6 is a perspective view showing how the sample vessel holder is being conveyed, specifically, a loading condition in which a sample vessel is loaded in the holder holding section.

FIG. 7 is a top view showing how the sample vessel holder is being conveyed, specifically, a loading condition in which a sample vessel is loaded in the holder holding section.

FIG. 8 is a perspective view showing how the sample vessel holder is being conveyed, specifically, a condition of the holder holding section being rotated with the sample vessel loaded therein.

FIG. 9 is a top view showing how the sample vessel holder is being conveyed, specifically, a condition of the holder holding section being rotated with the sample vessel loaded therein.

FIG. 16 is a perspective view schematically showing a representative configuration of a conveying unit according to a fourth embodiment of the present invention, which conveys the sample vessel holders only.

FIG. 17 is a top view schematically showing a representative configuration of the conveying unit according to the fourth embodiment of the present invention, which conveys the sample vessel holders only.

MODES FOR CARRYING OUT THE INVENTION

First Embodiment

A first embodiment of the present invention will be described below with reference to the accompanying drawings.

Figure 18:
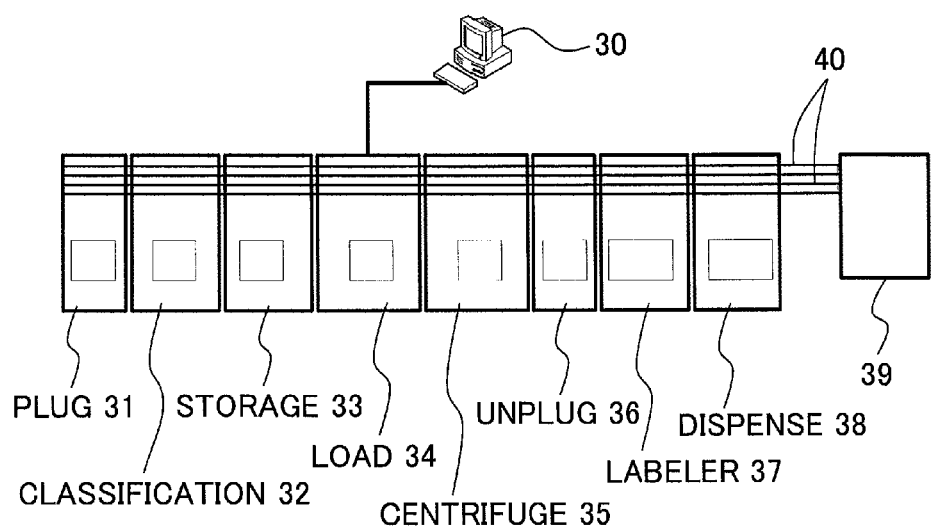
FIG. 18 is a schematic view showing a general configuration of a sample processing system according to an embodiment of the present invention.

FIG. 18 schematically shows a general configuration of a sample processing system according to the embodiment.

In FIG. 18, the sample processing system performs pre-processing for a biological sample, such as blood and urine (hereinafter referred to as a sample), subjected to analytical processing performed by an automatic analyzer 39. The sample processing system includes a loading module 34, a centrifuging module 35, an unplugging module 36, a dispensing module 38, a labeler 37, a plugging module 31, a storing module 33, a classifying module 32, a conveying unit 40, and a general control unit 30. Specifically, the loading module 34 assumes a section at which sample vessels storing therein samples are loaded into the sample processing system. The centrifuging module 35 centrifuges the loaded sample vessels. The unplugging module 36 unplugs the sample vessels that have been subjected to the centrifuging. The dispensing module 38 dispenses the sample from an unplugged sample vessel to second sample vessels (e.g., child sample vessels). The labeler 37 labels the second sample vessels in which the samples have been dispensed (e.g., affixing a bar code (label) indicating sample information). The plugging module 31 plugs the sample vessels. The storing module 33 stores unplugged sample vessels. The classifying module 32 classifies the second sample vessels in which the samples have been dispensed according to the label. The conveying unit 40 conveys the sample vessels (a sample vessel holder 1 to be described later and a sample vessel 17) between each components of 31 to 38 of the sample processing system and conveys the sample vessels to an automatic analyzer. The general control unit 30 generally controls operations of the sample processing system.

The conveying unit 40 according to the embodiment conveys, as appropriate, the sample vessel holder 1 to be described later and the sample vessel 17 held in the sample vessel holder 1 along a pre-processing system and in the automatic analyzer 39. The conveying unit 40 will be described below in detail with reference to the accompanying drawings.

Figure 1:
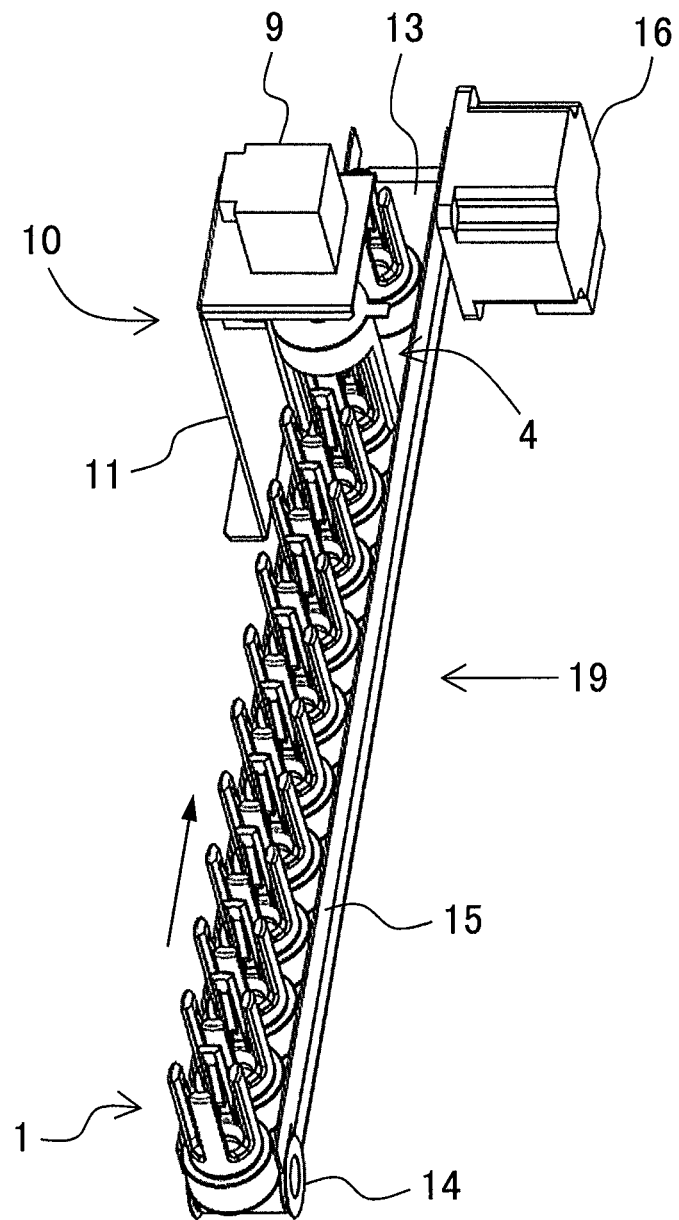
FIG. 1 is a perspective view showing a representative configuration of a conveying unit according to a first embodiment of the present invention.
Figure 2:
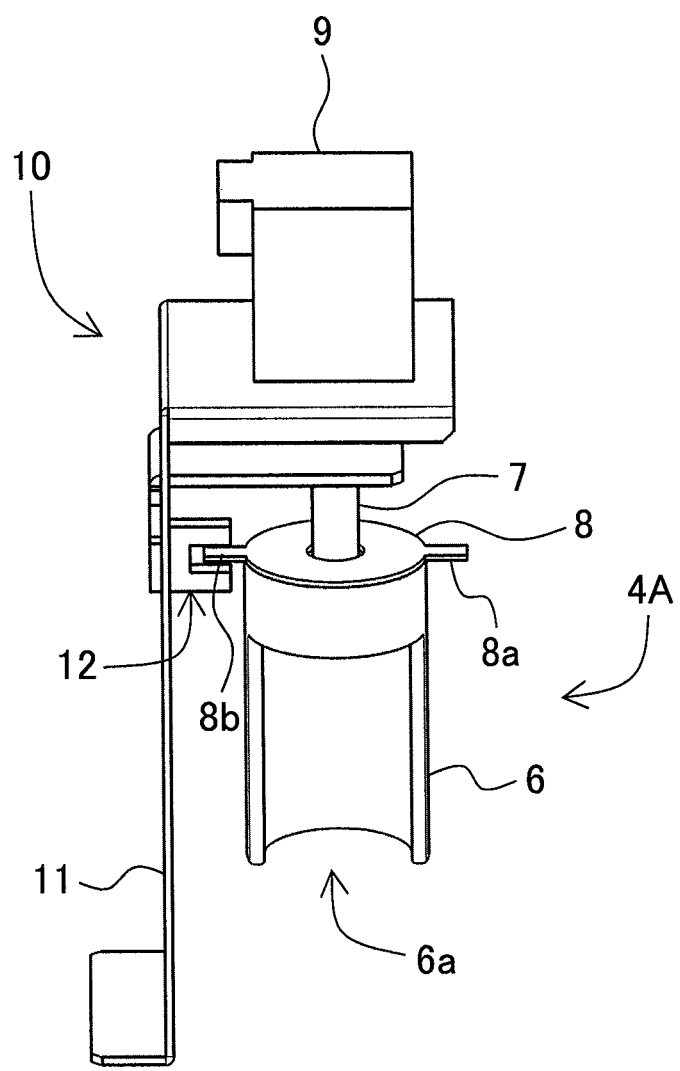
FIG. 2 is a side elevational view showing a holder holding mechanism according to the first embodiment of the present invention.
Figure 3:
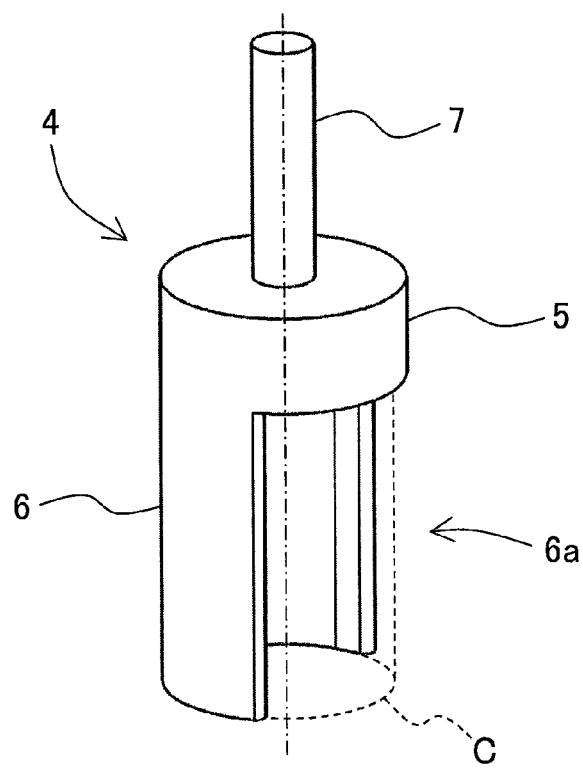
FIG. 3 is a side elevational view showing a holder holding section as extracted from the holder holding mechanism according to the first embodiment of the present invention.
Figure 4:
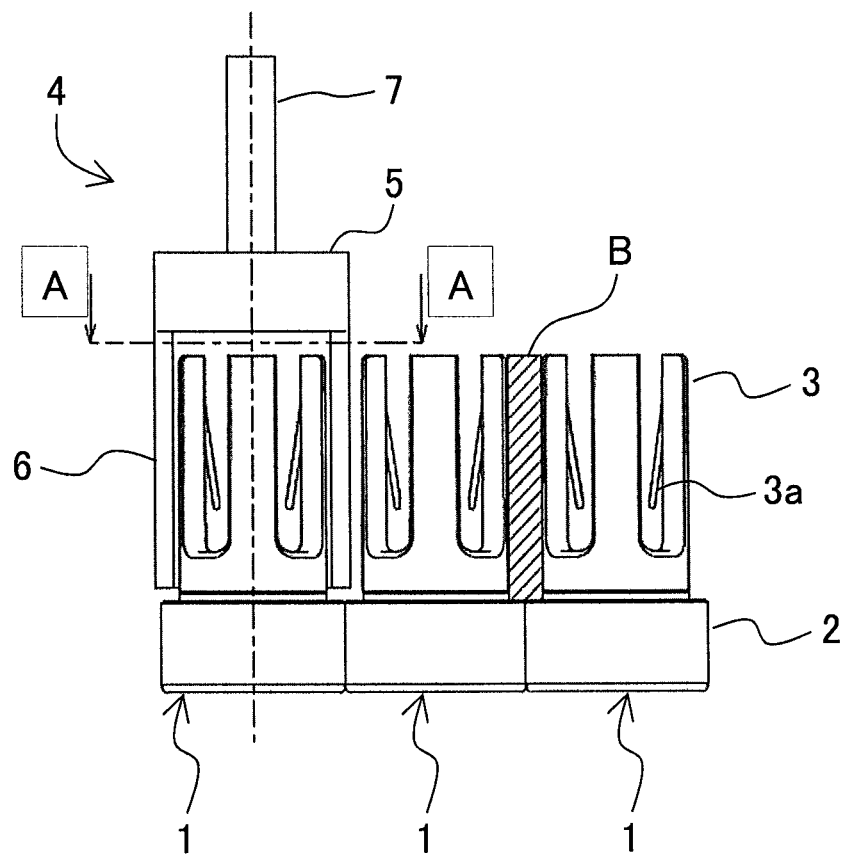
FIG. 4 is a side elevational view showing a relation in position and size between the holder holding section and a sample vessel holder according to the first embodiment of the present invention.
Figure 5:
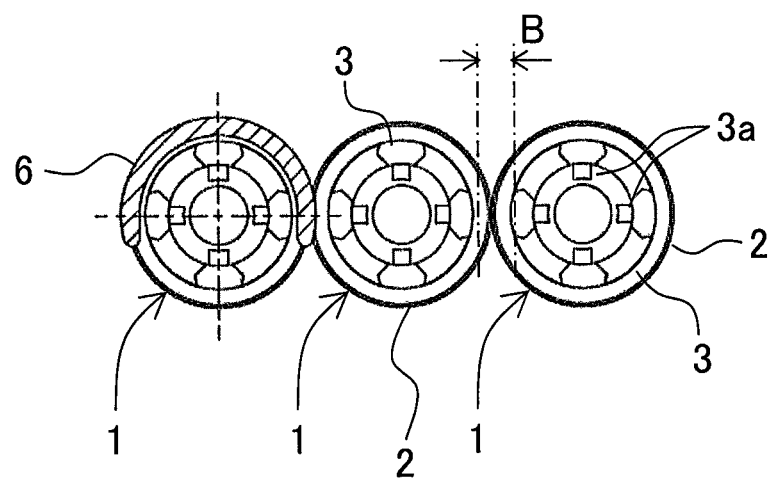
FIG. 5 is a top view showing a relation in position and size between the holder holding section and the sample vessel holder according to the first embodiment of the present invention.

A case will be described in which the conveying unit 40 conveys only the sample vessel holder 1. FIG. 1 is a perspective view showing schematically a representative configuration of the conveying unit 40 conveying only the sample vessel holder 1. FIG. 2 is a side elevational view showing a holder holding mechanism 10 as extracted from FIG. 1. FIG. 3 is a side elevational view showing a holder holding section 4 as extracted from FIG. 2. FIGS. 4 and 5 schematically illustrate a relation in position and size between the holder holding section 4 and the sample vessel holder 1 on a conveyor 19 in the holder holding mechanism 10, FIG. 4 being a side elevational view and FIG. 5 being a top view including a cross-sectional view taken along line A-A in FIG. 4.

In FIG. 1, the conveying unit 40 generally includes a conveyor 19 and the holder holding mechanism 10. Specifically, the conveyor 19 assumes a conveying path for the sample vessel holder 1 for holding therein the sample vessel 17 (see, for example, FIG. 12 to be later referred to). The holder holding mechanism 10 controls flow of the sample vessel holder 1 on the conveyor 19. It is noted that, in the following, the upper side and the lower side of FIG. 1 will be referred to as a downstream side and an upstream side of the conveying unit, respectively.

The conveyor 19 includes pulleys 14, a belt 13, a drive motor 16, and holder guides 15. The pulleys 14 (only one on the upstream side is shown) are rotatably disposed on both upstream and downstream ends of a frame not shown. The belt 13 is trained over the pulleys 14 on both ends. The drive motor 16 is coupled to the downstream pulley. The holder guides 15 disposed on both sides of the belt 13 prevent the sample vessel holder 1 conveyed on the belt 13 from being laterally deviated. Driving the downstream pulley with the drive motor 16 causes the belt 13 to be circulatingly driven between the upstream and downstream pulleys 14, resulting in the sample vessel holder 1 placed on the belt 13 being conveyed to the downstream side along the holder guides 15. It is noted that a case in which an upper surface of the belt 13 moves toward the downstream side is forward drive, while a case in which the upper surface of the belt 13 moves toward the upstream side is reverse drive.

As shown in, for example, FIG. 4, the sample vessel holder 1 according to the embodiment includes a disk-shaped base section 2 and a sample vessel holding section 3. The base section 2 is disposed such that a central axis thereof extends in a vertical direction. The sample vessel holding section 3 is formed above, and coaxially with, the base section 2 so that the sample vessel holding section 3 has an outside diameter smaller than that of the base section 2. The sample vessel holding section 3 holds the sample vessel 17 in an upright posture.

The base section 2 is formed to be lower in height than a height from a conveying surface of the conveyor 19 to a lower end of the holder holding section 4 (to be described later) disposed on the conveying path. Additionally, the base section 2 is formed to have a weight such that a center of gravity thereof is low enough to ensure stability on the conveyor 19 of the entire sample vessel holder 1 including the sample vessel 17 held in the sample vessel holding section 3. The base section 2 has an identification sign (e.g., an RFID) for identifying a specific sample vessel holder 1 (specifically, identifying the sample vessel 17 held in the sample vessel holder 1) to thereby enable identification by a detector (not shown) on the conveying path.

The sample vessel holding section 3 has an opening at an upper portion thereof, the opening receiving the sample vessel 17 inserted thereinto. The sample vessel holding section 3 further has a plurality of gripping protrusions 3a disposed on an inner periphery thereof, the gripping protrusions 3a holding the sample vessel 17 laterally. Inserting the sample vessel 17 from above into the sample vessel holding section 3 causes the sample vessel 17 to be held by the gripping protrusions 3a, so that the sample vessel 17 is held in the sample vessel holder 1 in an upright posture.

When a plurality of sample vessel holders 1, each sample vessel holder 1 being configured as described above, are arrayed with no gap therebetween on the conveyor 19 as the conveying path, the base section 2 of each sample vessel holder 1 has side surfaces in contact with each other and a gap B is formed between each pair of adjacent sample vessel holding sections 3 of the sample vessel holders 1.

In FIGS. 1 to 3, the holder holding mechanism 10 includes a base 11, the holder holding section 4 disposed on the conveyor 19 as the conveying path, and a drive motor 9 that rotatably drives the holder holding section 4 in a horizontal direction.

The holder holding section 4 includes a shaft 7, a holding plate base 5, and a holding plate 6. The shaft 7 having a central axis extending in the vertical direction is rotatably disposed on the base 11. The holding plate base 5 is disposed at a lower end of the shaft 7. The holding plate 6 is disposed on the holding plate base 5 so as to extend along an outer peripheral portion of a columnar space C having the central axis of the shaft 7 as its center. Rotatably driving the shaft 7 with the drive motor 9 causes the holding plate 6 to move circumferentially along the outer peripheral portion of the columnar space C. A rotational angle of the drive motor 9 can be controlled based on a control signal from the general control unit 30. The drive motor 9 is exemplarily a stepping (pulse) motor. The holding plate 6 is disposed so as to extend circumferentially along the outer peripheral portion of the columnar space C. The holding plate 6 is disposed so as to exist at least at an opposite position of the outer peripheral portion of the columnar space C. A portion between circumferential ends of the holding plate 6 will hereinafter be referred to as an opening 6a.

A plate 8 is fixed to an upper portion of the holding plate base 5. The plate 8 has direction detecting protrusions 8a, 8b protruding outwardly in a radial direction. In addition, a sensor 12 is fixed to the base 11 at a position past which the direction detecting protrusions 8a, 8b move as the holder holding section 4 rotates circumferentially. The direction detecting protrusions 8a, 8b of the plate 8 are disposed at positions symmetrical about the shaft 7 such that the direction detecting protrusion 8b moves past, and is detected by, the sensor 12 when the opening 6a faces the upstream side of the conveyor 19 and the direction detecting protrusion 8a moves past, and is detected by, the sensor 12 when the opening 6a faces the downstream side of the conveyor 19. A detection signal of the sensor 12 is sent to the general control unit 30.

The holding plate base 5 of the holder holding section 4 is disposed so as to be higher in level than a height of an upper end of the sample vessel holder 1 placed on the conveying path from the conveying surface of the conveyor 19. Additionally, the opening 6a in the holder holding section 4 is formed to be wider than a diameter of the sample vessel holding section 3 of the sample vessel holder 1.

As shown in FIGS. 4 and 5, an inside diameter of the holding plate 6 or, to state the foregoing differently, an inside diameter of a cylindrical space through which the holding plate 6 passes as the holder holding section 4 rotates about the shaft 7 is formed to be greater than an outside diameter of the sample vessel holding section 3 of the sample vessel holder 1. An outside diameter of the holding plate 6 or, to state the foregoing differently, an outside diameter of the cylindrical space through which the holding plate 6 passes as the holder holding section 4 rotates about the shaft 7 is formed in such a size as, in a condition of including one of the sample vessel holders 1 disposed adjacent to each other (the condition shown in, for example, FIGS. 4 and 5), not to be in contact with an outer periphery of the sample vessel holding section 3 of the adjacent sample vessel holder 1. Thus, when the holder holding section 4 is rotated about the shaft 7 under this condition (the condition of, for example, FIGS. 4 and 5), one circumferential end of the holding plate 6 moves past the gap B formed between two adjacent sample vessel holders 1.

Basic operations of the sample processing system and the conveying unit according to the embodiment will be described below.

Figure 10:
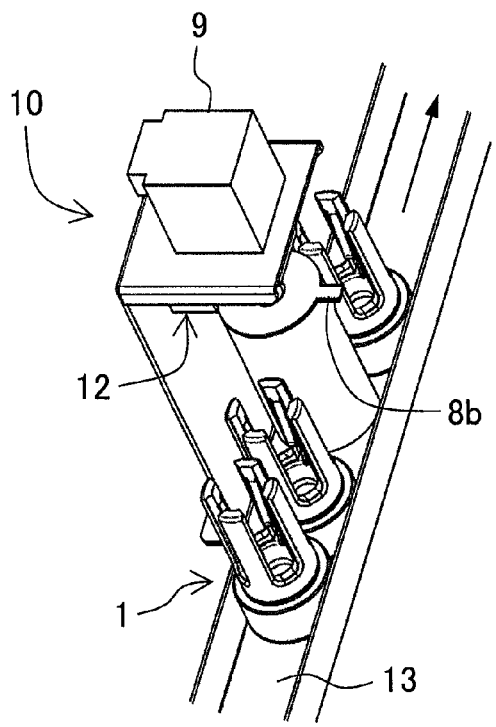
FIG. 10 is a perspective view showing how the sample vessel holder is being conveyed, specifically, an unloading condition in which the sample vessel is unloaded from the holder holding section.
Figure 11:
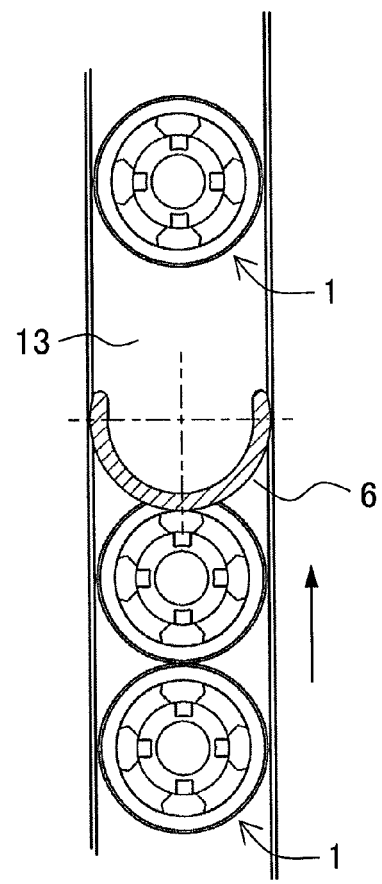
FIG. 11 is a top view showing how the sample vessel holder is being conveyed, specifically, an unloading condition in which the sample vessel is unloaded from the holder holding section.

FIGS. 6 to 11 illustrate how the sample vessel holders 1 are conveyed in the conveying unit of this embodiment. FIGS. 6 and 7 show a loading condition in which a sample vessel is loaded in the holder holding section, FIG. 6 being a perspective view and FIG. 7 being a top view. FIGS. 8 and 9 show a condition of the holder holding section being rotated with the sample vessel loaded therein, FIG. 8 being a perspective view and FIG. 9 being a top view. FIGS. 10 and 11 show an unloading condition in which the sample vessel is unloaded from the holder holding section, FIG. 10 being a perspective view and FIG. 11 being a top view.

When a pre-processing command relative to a sample to be subject to analytical processing by the automatic analyzer 39 is applied to the general control unit 30, the sample processing system according to the embodiment uses the conveying unit 40 to perform conveying processing for a sample vessel loaded in the loading module 34 among the centrifuging module 35, the unplugging module 36, the dispensing module 38, the labeler 37, the plugging module 31, the storing module 33, the classifying module 32, and the automatic analyzer.

The conveying unit 40 first causes the opening 6a in the holder holding section 4 in the holder holding mechanism 10 to face toward the upstream side of the conveyor 19 (specifically, sets up a condition in which the sensor 12 detects the direction detecting protrusion 8b). Under this condition, the belt 13 of the conveyor 19 is circulatingly driven in the forward direction to thereby place the sample vessel holder 1 on the upstream side of the holder holding mechanism 10. This causes the belt 13 to convey the sample vessel holder 1 toward the downstream side, so that the sample vessel holder 1 is loaded into an inside of the holder holding section 4 through the opening 6a in the holder holding section 4 (loaded condition). The sample vessel holding section 3 of the sample vessel holder 1 then contacts an inner periphery on the downstream side of the holder holding section 4. This brings the sample vessel holder 1 to a stop as a result of the sample vessel holder 1 resisting to a friction force acting on the base section 2 thereof from the belt 13. When a plurality of sample vessel holders 1 is then placed on the upstream side of the holder holding mechanism 10, the base section 2 of each of the sample vessel holders 1 contacts the base section of a corresponding sample vessel holder 1 on the downstream side, so that the sample vessel holder 1 is stopped as a result of its resisting to the friction force from the belt 13 (see FIGS. 6 and 7).

Next, the holder holding section 4 is rotated about the shaft 7 by the drive motor 9. As described earlier, the holding plate 6 is disposed so as to exist at least at an opposite position of the outer peripheral portion of the columnar space C. Thus, while the sample vessel holding section 3 of the sample vessel holder 1 maintains a condition of being in contact with the inner periphery of the holding plate 6 of the holder holding section 4, one circumferential end of the holding plate 6 moves past the gap B formed between the sample vessel holder 1 inside the holder holding section 4 and the sample vessel holder 1 adjacent thereto on the upstream side (see FIGS. 8 and 9).

When the opening 6a in the holder holding section 4 in the holder holding mechanism 10 then faces toward the downstream side of the conveyor 19 (specifically, when a condition is set up in which the sensor 12 detects the direction detecting protrusion 8a), the sample vessel holder 1 is conveyed toward the downstream side by the belt 13 and unloaded via the opening 6a in the holder holding section 4 out of the holder holding section 4 (unloaded condition). At this time, the sample vessel holder 1 on the upstream side of the holder holding section 4 is brought to a stop as a result of the sample vessel holder 1 resisting to the friction force acting on the base section 2 thereof from the belt 13 because of the sample vessel holding section 3 contacting an outer periphery on the upstream side of the holder holding section 4. The sample vessel holders 1 placed on the upstream side of the holder holding mechanism 10 are stopped as a result of their resisting to the friction force from the belt 13 when the base section 2 of each of the sample vessel holders 1 contacts the base section of a corresponding sample vessel holder 1 on the downstream side (see FIGS. 10 and 11).

Then, the drive motor 9 causes the holder holding section 4 to rotate about the shaft 7 to thereby bring the opening 6a in the holder holding section 4 in the holder holding mechanism 10 into a position at which the opening 6a faces toward the upstream side of the conveyor 19 (specifically, a condition in which the sensor 12 detects the direction detecting protrusion 8b). As a result, the sample vessel holder 1 is conveyed toward the downstream side by the belt 13 and is then loaded into the inside of the holder holding section 4 via the opening 6a in the holder holding section 4 (loaded condition).

As described above, the conveying unit 40 of the embodiment unloads the sample vessel holders 1 placed on the belt 13 of the conveyor 19 one by one toward the downstream side as necessary, thereby controlling the flow of the sample vessel holders 1.

Figure 12:
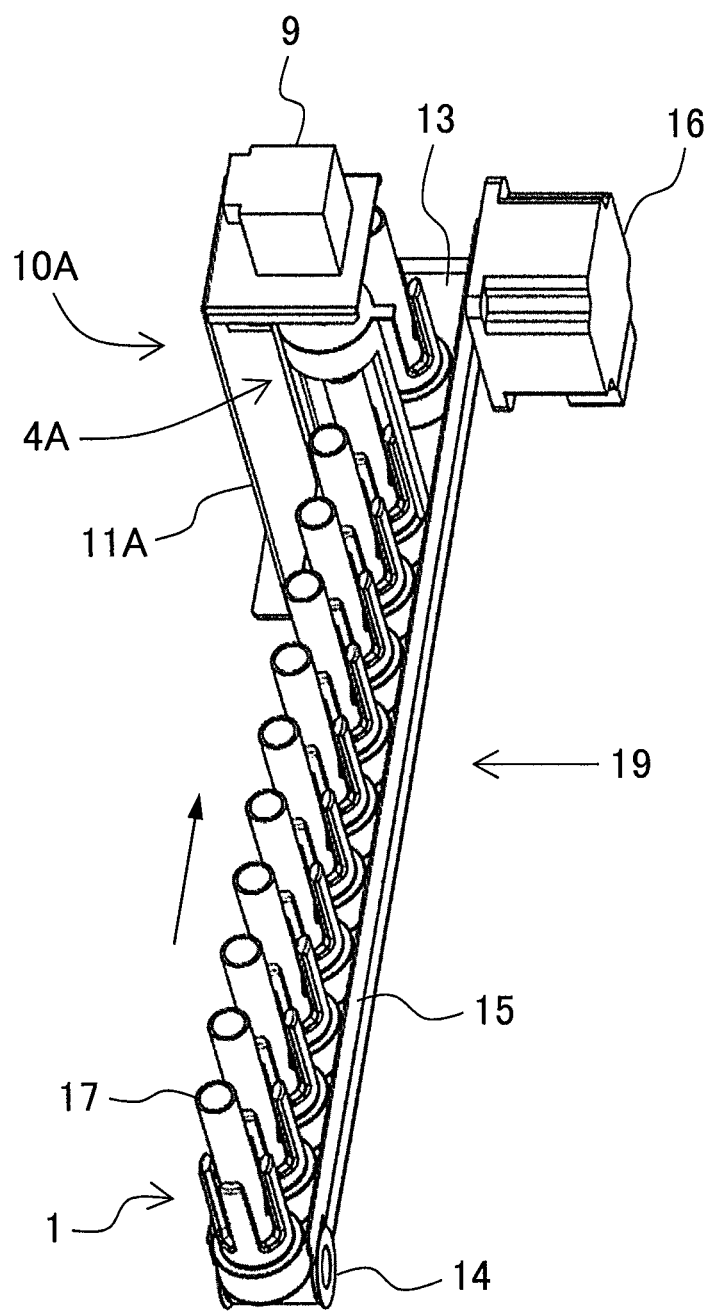
FIG. 12 is a perspective view showing schematically a representative configuration of the conveying unit when the conveying unit conveys the sample vessel holder in which the sample vessel is held.
Figure 13:
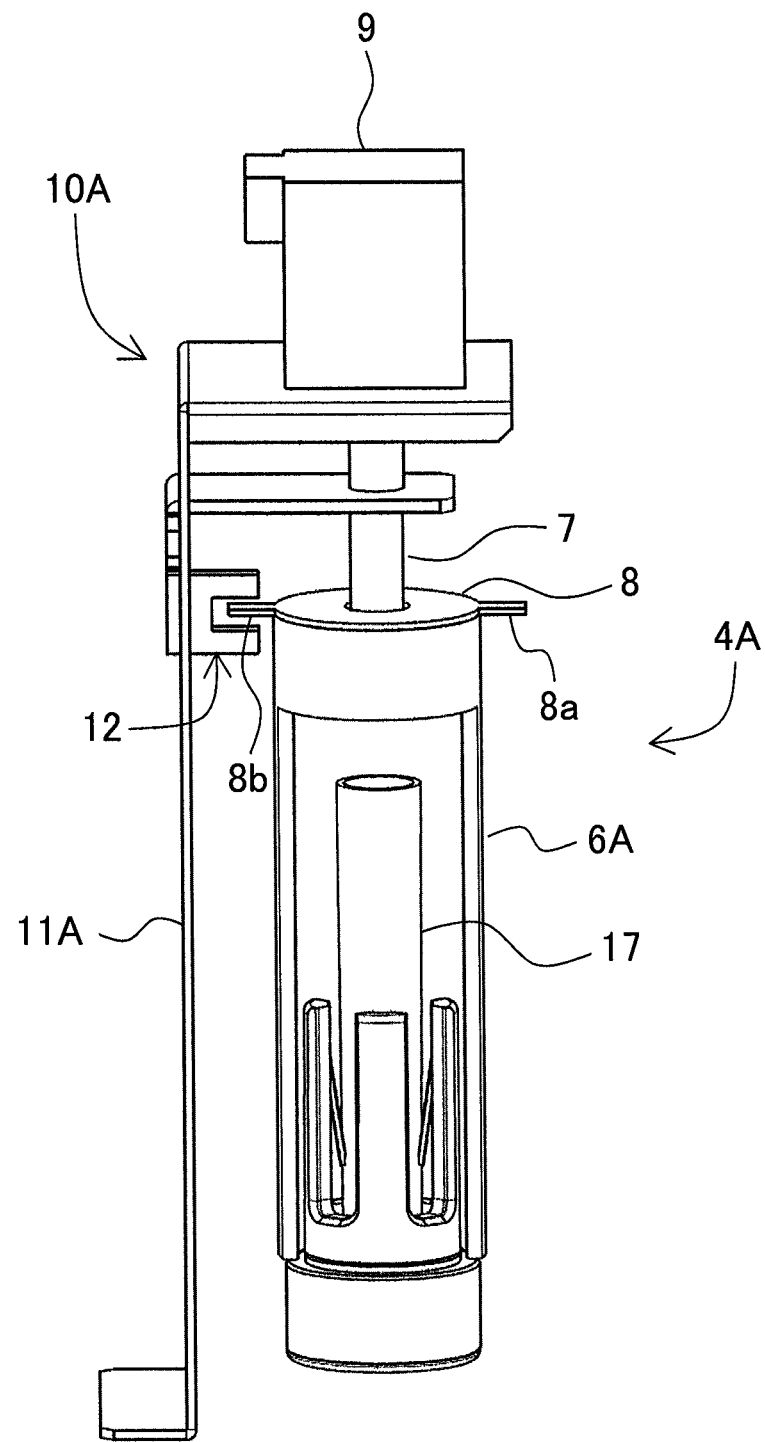
FIG. 13 is a side elevational view showing a holder holding mechanism as extracted from FIG. 12.

A case will be described below in which the conveying unit 40 conveys the sample vessel holder 1 that holds therein the sample vessel 17. FIG. 12 is a perspective view showing schematically a representative configuration of the conveying unit 40 when the conveying unit 40 conveys the sample vessel holder 1 in which the sample vessel 17 is held. FIG. 13 is a side elevational view showing a holder holding mechanism 10A as extracted from FIG. 12.

In FIG. 12, the conveying unit 40 generally includes the conveyor 19 that assumes the conveying path for the sample vessel holder 1 holding therein the sample vessel 17 (hereinafter jointly referred to simply as the sample vessel holder 1) and the holder holding mechanism 10A that controls the flow of the sample vessel holder 1 on the conveyor 19.

The conveyor 19 includes the pulleys 14, the belt 13, the drive motor 16, and the holder guides 15. The pulleys 14 (only one on the upstream side is shown) are rotatably disposed on both upstream and downstream ends of a frame not shown. The belt 13 is trained over the pulleys 14 on both ends. The drive motor 16 is coupled to the downstream pulley. The holder guides 15 disposed on both sides of the belt 13 prevent the sample vessel holder 1 conveyed on the belt 13 from being laterally deviated. Driving the downstream pulley with the drive motor 16 causes the belt 13 to be circulatingly driven between the upstream and downstream pulleys 14, resulting in the sample vessel holder 1 and the sample vessel 17 placed on the belt 13 being conveyed to the downstream side along the holder guides 15. It is noted that a case in which the upper surface of the belt 13 moves toward the downstream side is forward drive, while a case in which the upper surface of the belt 13 moves toward the upstream side is reverse drive.

In FIG. 13, the holder holding mechanism 10A includes a base 11A, a holder holding section 4A disposed on the conveyor 19 as the conveying path, and a drive motor 9 that rotatably drives the holder holding section 4A in a horizontal direction.

The holder holding section 4A includes a shaft 7, a holding plate base 5, and a holding plate 6A. The shaft 7 having a central axis extending in the vertical direction is rotatably disposed on the base 11A. The holding plate base 5 is disposed at a lower end of the shaft 7. The holding plate 6A is disposed on the holding plate base 5 so as to extend along an outer peripheral portion of a columnar space C having the central axis of the shaft 7 as its center. Rotatably driving the shaft 7 with the drive motor 9 causes the holding plate 6A to move circumferentially along the outer peripheral portion of the columnar space C. The holding plate 6A is disposed so as to extend circumferentially along the outer peripheral portion of the columnar space C. The holding plate 6A is disposed so as to exist at least at an opposite position of the outer peripheral portion of the columnar space C.

The holding plate base 5 of the holder holding section 4A is disposed so as to be higher in level than a height of an upper end of the sample vessel holder 1 and the sample vessel 17 placed on the conveying path, from the conveying surface of the conveyor 19.

Other arrangements and basic operations are the same as those with the holder holding mechanism 10 that conveys only the sample vessel holder 1. Specifically, the conveying unit 40 unloads the sample vessel holders 1, each holding therein a sample vessel 17, placed on the belt 13 of the conveyor 19 one by one toward the downstream side as necessary, thereby controlling the flow of the sample vessels 17 and the sample vessel holders 1.

Effects will be described of the embodiment having the arrangements as described above.

To achieve labor saving and higher speed in testing, sample processing systems that automatically perform pre-processing and conveyance of samples to be loaded in automatic analyzers are used in clinical laboratory settings in which qualitative and quantitative analyses of biological samples such as blood and urine are conducted. Such sample processing systems perform various types of processing for samples stored in, for example, sample vessels and loaded in the systems. Among known techniques relating to these types of processing, one automatic unplugging apparatus operates as follows. Specifically, out of a plurality of test tubes held in an upright posture in one row in a test tube rack, the automatic unplugging apparatus simultaneously clamps plug bodies of every other test tube and moves upwardly to thereby remove the plug bodies. The automatic unplugging apparatus then simultaneously clamps plug bodies of the rest of the test tubes and moves upwardly to thereby remove the plug bodies from the rest of the test tubes. Conventional sample processing systems perform pre-processing or the like for the samples by conveying a rack that holds a plurality of sample vessels as in the known art. A need, however, exists in recent years for individually conveying a plurality of sample vessels to thereby concurrently perform different analysis processes, thus responding to changes and developments in analysis techniques and further improving processing efficiency.

In contrast, the present embodiment is configured to include the holder holding mechanism disposed at a position at which the sample vessel holding section on the conveying path that conveys thereon the sample vessel holder passes, the holder holding mechanism including the holding plate disposed so as to extend along the outer peripheral portion of the columnar space having a central axis extending in the vertical direction. The embodiment is configured so as to switch between conveyable state and not conveyable state of the sample vessel holder, which is conveyed along the conveying path, toward the downstream side by the movement of the holding plate in the circumferential direction. This enables individual conveyance processing to be performed for each of sample vessels, thus responding to changes and developments in analysis techniques and improving processing efficiency.

Second Embodiment

A second embodiment of the present invention will be described below with reference to the accompanying drawings.

This embodiment is configured so as to control the flow of sample vessel holders 1 by selectively unloading a sample vessel holder 1 and a sample vessel 17 one by one to the downstream side as necessary as selected from among a plurality of sample vessel holders 1 and sample vessels 17, which are placed on a belt 13 of a conveyor 19 and on a belt 113 of a sub-conveyor 119 and conveyed from two directions.

Figure 14:
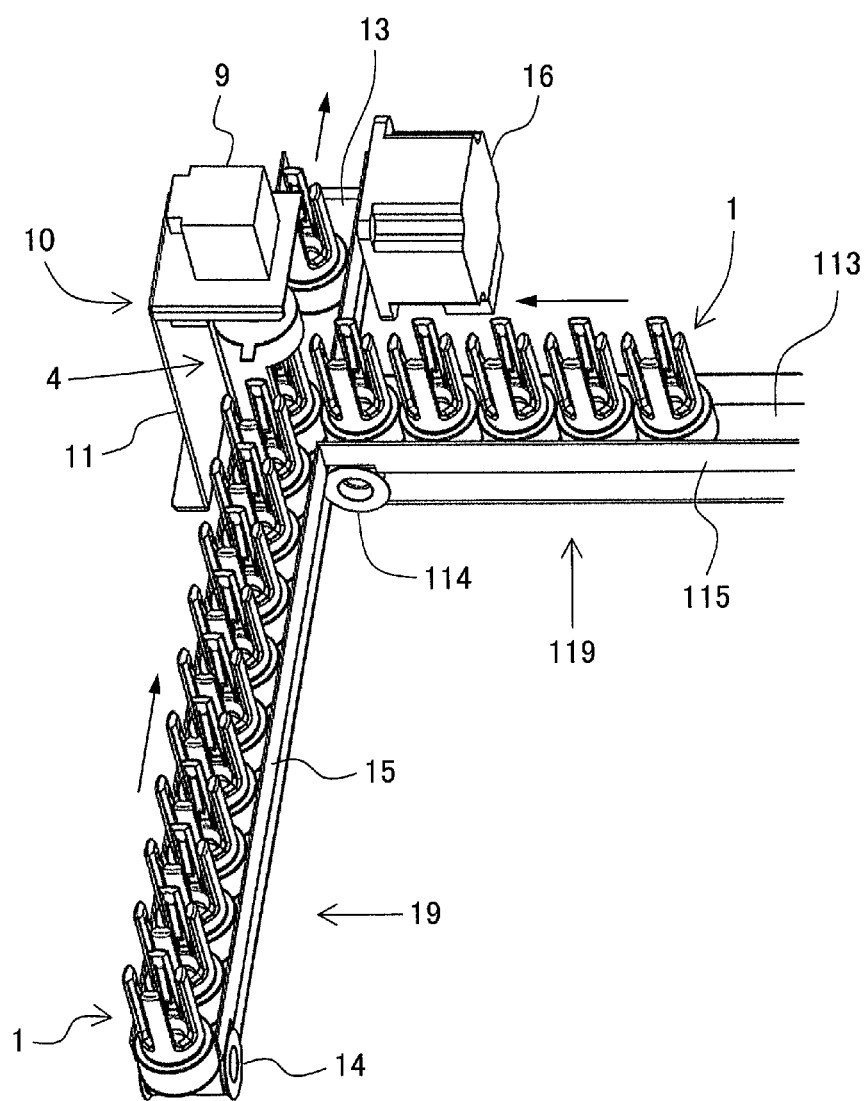
FIG. 14 is a perspective view schematically showing a representative configuration of a conveying unit according to a second embodiment of the present invention, which conveys the sample vessel holders only.

FIG. 14 is a perspective view schematically showing a representative configuration of a conveying unit according to this embodiment conveying the sample vessel holders only. Like or corresponding parts are identified by the same reference numerals as those used in the first embodiment and descriptions for those parts will not be duplicated.

In FIG. 14, the conveying unit 40 of this embodiment generally includes the conveyor 19, the sub-conveyor 119, and a holder holding mechanism 10. Specifically, the conveyor 19 assumes a conveying path for the sample vessel 17 and the sample vessel holder 1 for holding therein the sample vessel 17. The sub-conveyor 119 conveys the sample vessel holder 1 onto the conveyor 19 from a lateral direction of the conveyor 19. The holder holding mechanism 10 is disposed at a portion at which the conveyor 19 merges with the sub-conveyor 119 and controls flow of the sample vessel holder 1.

The conveyor 19 includes pulleys 14, the belt 13, a drive motor 16, and holder guides 15. The pulleys 14 (only one on the upstream side is shown) are rotatably disposed on both upstream (the lower side in FIG. 14) and downstream (the upper side in FIG. 14) ends of a frame not shown. The belt 13 is trained over the pulleys 14 on both ends. The drive motor 16 is coupled to the downstream pulley. The holder guides 15 disposed on both sides of the belt 13 prevent the sample vessel holder 1 conveyed on the belt 13 from being laterally deviated. Driving the downstream pulley with the drive motor 16 causes the belt 13 to be circulatingly driven between the upstream and downstream pulleys 14, resulting in the sample vessel holder 1 placed on the belt 13 being conveyed to the downstream side along the holder guides 15. It is noted that a case in which an upper surface of the belt 13 moves toward the downstream side is forward drive, while a case in which the upper surface of the belt 13 moves toward the upstream side is reverse drive.

The sub-conveyor 119 includes pulleys 114, the belt 113, a drive motor (not shown), and holder guides 115. The pulleys 114 (only one on the downstream side is shown) are rotatably disposed on both upstream (the right-hand side in FIG. 14) and downstream (the left-hand side in FIG. 14) ends of a frame not shown. The belt 113 is trained over the pulleys 114 on both ends. The drive motor is coupled to the upstream pulley. The holder guides 115 disposed on both sides of the belt 113 prevent the sample vessel holder 1 conveyed on the belt 113 from being laterally deviated. The sub-conveyor 119 has a downstream end portion disposed so as to be opposed to and close to a lateral side (a portion partially removed from the holder guide 15) of the conveyor 19. Driving the upstream pulley with the drive motor causes the belt 113 to be circulatingly driven between the upstream and downstream pulleys 114, resulting in the sample vessel holder 1 placed on the belt 113 being conveyed to the downstream side, specifically, the side of the conveyor 19 along the holder guides 115. It is noted that a case in which an upper surface of the belt 113 moves toward the downstream side is forward drive, while a case in which the upper surface of the belt 113 moves toward the upstream side is reverse drive.

The holder holding mechanism 10 is disposed at the portion at which the conveyor 19 merges with the sub-conveyor 119. The holder holding mechanism 10 includes a base 11, a holder holding section 4, and a drive motor 9. The holder holding section 4 is disposed at a portion of the conveyor 19 as the conveying path at which the conveyor 19 merges with the sub-conveyor 119. The drive motor 9 rotatably drives the holder holding section 4 in the horizontal direction.

Other arrangements are the same as those in the first embodiment of the present invention.

Basic operations of the conveying unit according to the embodiment will be described below.

To unload the sample vessel holder 1 placed on the conveyor 19, the conveying unit first causes an opening 6a in the holder holding section 4 in the holder holding mechanism 10 to face toward the upstream side of the conveyor 19 (specifically, sets up a condition in which a sensor 12 detects a direction detecting protrusion 8b). Under this condition, the belt 13 of the conveyor 19 and the belt 113 of the sub-conveyor 119 are circulatingly driven in the forward direction to thereby place the sample vessel holder 1 on the upstream sides of the conveyor 19 and of the sub-conveyor 119 with respect to the holder holding mechanism 10. This causes the belts 13 and 113 to convey the sample vessel holder 1 toward the downstream side.

At this time, the sample vessel holder 1 placed on the conveyor 19 is loaded into an inside of the holder holding section 4 through the opening 6a in the holder holding section 4 (loaded condition). A sample vessel holding section 3 of the sample vessel holder 1 then contacts an inner periphery of a holding plate 6 on the downstream side of the holder holding section 4. This brings the sample vessel holder 1 to a stop as a result of the sample vessel holder 1 resisting to a friction force acting on a base section 2 thereof from the belt 13. When a plurality of sample vessel holders 1 is then placed on the upstream side of the holder holding mechanism 10, the base section 2 of each of the sample vessel holders 1 contacts the base section of a corresponding sample vessel holder 1 on the downstream side, so that the sample vessel holder 1 is stopped as a result of its resisting to the friction force from the belt 13. For the sample vessel holders 1 placed on the sub-conveyor 119, the base section of the sample vessel holder 1 on the downstream side contacts the base section 2 of the sample vessel holder 1 loaded in the inside of the holder holding section 4 and the sample vessel holder 1 on the downstream side is stopped as a result of its resisting to the friction force from the belt 113.

Next, the holder holding section 4 is rotated about a shaft 7 by the drive motor 9 in a clockwise direction as viewed from above, specifically, such that the opening 6a faces in a direction opposite to the sub-conveyor 119. The holding plate 6 is disposed so as to exist at least at an opposite position of an outer peripheral portion of a columnar space C. Thus, while the sample vessel holding section 3 of the sample vessel holder 1 maintains a condition in which it is in contact with the inner periphery of the holding plate 6 of the holder holding section 4, one circumferential end of the holding plate 6 moves past a gap B formed between the sample vessel holder 1 inside the holder holding section 4 and the sample vessel holder 1 adjacent thereto on the upstream side.

When the opening 6a in the holder holding section 4 in the holder holding mechanism 10 then faces toward the downstream side of the conveyor 19 (specifically, when a condition is set up in which the sensor 12 detects a direction detecting protrusion 8a), the sample vessel holder 1 is conveyed toward the downstream side by the belt 13 and unloaded via the opening 6a in the holder holding section 4 out of the holder holding section 4 (unloaded condition). At this time, the sample vessel holder 1 on the upstream side of the holder holding section 4 is brought to a stop as a result of the sample vessel holder 1 resisting to the friction force acting on the base section 2 thereof from the belt 13 because of the sample vessel holding section 3 contacting an outer periphery on the upstream side of the holder holding section 4. The sample vessel holders 1 placed on the upstream side of the holder holding mechanism 10 are stopped as a result of their resisting to the friction force from the belt 13 when the base section 2 of each of the sample vessel holders 1 contacts the base section of a corresponding sample vessel holder 1 on the downstream side. Additionally, the sample vessel holders 1 placed on the upstream side of the holder holding mechanism 10 on the sub-conveyor 119 are stopped as a result of their resisting to the friction force from the belt 13 acting on the base sections 2 when the sample vessel holding section 3 contacts the outer periphery of the holder holding section 4 on the upstream side.

To unload the sample vessel holder 1 placed on the conveyor 19 from this condition (the condition in which the opening 6a faces toward the downstream side in the conveyor 19), the holder holding section 4 is rotated about the shaft 7 by the drive motor 9 in a counterclockwise direction as viewed from above, specifically, such that the opening 6a faces in the direction opposite to the sub-conveyor 119, to thereby cause the opening 6a in the holder holding section 4 in the holder holding mechanism 10 to face toward the upstream side of the conveyor 19 (specifically, a condition is set up in which the sensor 12 detects the direction detecting protrusion 8b). This allows the sample vessel holder 1 to be conveyed toward the downstream side by the belt 13, so that the sample vessel holder 1 is loaded into the inside of the holder holding section 4 through the opening 6a in the holder holding section 4 (loaded condition).

To unload the sample vessel holder 1 placed on the sub-conveyor 119, the conveying unit causes, with the sample vessel holder 1 not contained inside the holder holding section 4, the opening 6a in the holder holding section 4 in the holder holding mechanism 10 to face toward the side of the sub-conveyor 119 (specifically, sets up a condition in which the holder holding section 4 is rotated 90° in the clockwise direction as viewed from above from the condition in which the sensor 12 detects the direction detecting protrusion 8a). Under this condition, the belt 13 of the conveyor 19 and the belt 113 of the sub-conveyor 119 are circulatingly driven in the forward direction to thereby place the sample vessel holder 1 on the upstream sides of the conveyor 19 and of the sub-conveyor 119 with respect to the holder holding mechanism 10. This causes the belts 13, 113 to convey the sample vessel holder 1 toward the downstream side.

At this time, the sample vessel holder 1 placed on the sub-conveyor 119 is loaded into the inside of the holder holding section 4 through the opening 6a in the holder holding section 4 (loaded condition). The sample vessel holding section 3 of the sample vessel holder 1 then contacts the inner periphery of the holding plate 6 on the downstream side, in the conveyor 19, of the holder holding section 4. This brings the sample vessel holder 1 to a stop as a result of the sample vessel holder 1 resisting to the friction force acting on the base section 2 thereof from the belt 13. When a plurality of sample vessel holders 1 is additionally placed on the upstream side of the holder holding mechanism 10 in the sub-conveyor 119, the base section 2 of each of the sample vessel holders 1 contacts the base section of a corresponding sample vessel holder 1 on the downstream side, so that the sample vessel holder 1 is stopped as a result of its resisting to the friction force from the belt 113. For the sample vessel holders 1 placed on the conveyor 19, the base section of the sample vessel holder 1 on the downstream side contacts the base section 2 of the sample vessel holder 1 loaded in the inside of the holder holding section 4 and the sample vessel holder 1 on the downstream side is stopped as a result of its resisting to the friction force from the belt 13.

Next, the holder holding section 4 is rotated about the shaft 7 by the drive motor 9 in the counterclockwise direction as viewed from above, specifically, such that the opening 6a faces toward the downstream side of the conveyor 19. The holding plate 6 is disposed so as to exist at least at an opposite position of the outer peripheral portion of the columnar space C. Thus, while the sample vessel holding section 3 of the sample vessel holder 1 maintains a condition in which it is in contact with the inner periphery of the holding plate 6 of the holder holding section 4, one circumferential end of the holding plate 6 moves past the gap B formed between the sample vessel holder 1 inside the holder holding section 4 and the sample vessel holder 1 adjacent thereto on the upstream side in the sub-conveyor 119.

When the opening 6a in the holder holding section 4 in the holder holding mechanism 10 then faces toward the downstream side of the conveyor 19 (specifically, when a condition is set up in which the sensor 12 detects the direction detecting protrusion 8a), the sample vessel holder 1 is conveyed toward the downstream side by the belt 13 and unloaded via the opening 6a in the holder holding section 4 out of the holder holding section 4 (unloaded condition). At this time, the sample vessel holder 1 on the upstream side of the holder holding section 4 is brought to a stop as a result of the sample vessel holder 1 resisting to the friction force acting on the base section 2 thereof from the belt 13 because of the sample vessel holding section 3 contacting the outer periphery on the upstream side of the holder holding section 4. The sample vessel holders 1 placed on the upstream side of the holder holding mechanism 10 are stopped as a result of their resisting to the friction force from the belt 13 when the base section 2 of each of the sample vessel holders 1 contacts the base section of a corresponding sample vessel holder 1 on the downstream side. Additionally, the sample vessel holders 1 placed on the upstream side of the holder holding mechanism 10 on the sub-conveyor 119 are stopped as a result of their resisting to the friction force from the belt 13 acting on the base sections 2 when the sample vessel holding section 3 contacts the outer periphery of the holder holding section 4 on the upstream side.

To unload the sample vessel holder 1 placed on the sub-conveyor 119 from this condition (the condition in which the opening 6a faces toward the downstream side in the conveyor 19), the holder holding section 4 is rotated about the shaft 7 by the drive motor 9 in the clockwise direction as viewed from above, specifically, such that the opening 6a faces toward the sub-conveyor 119, to thereby cause the opening 6a in the holder holding section 4 in the holder holding mechanism 10 to face toward the sub-conveyor 119. This allows the sample vessel holder 1 to be conveyed toward the downstream side by the belt 113, so that the sample vessel holder 1 is loaded into the inside of the holder holding section 4 through the opening 6a in the holder holding section 4 (loaded condition).

As described above, the conveying unit of this embodiment selectively unloads one sample vessel holder 1 to the downstream side one by one as necessary as selected from among a plurality of sample vessel holders 1 placed on the belt 13 of the conveyor 19 and on the belt 113 of the sub-conveyor 119, to thereby control the flow of the sample vessel holders 1.

Other operations are the same as those in the first embodiment.

The same effects as those achieved in the first embodiment can also be achieved in this embodiment having the arrangements as described above.

Third Embodiment

A third embodiment of the present invention will be described below with reference to the accompanying drawings.

This embodiment is configured so as to control the flow of sample vessel holders 1 by selectively unloading, as selected from among a plurality of sample vessel holders 1 and sample vessels 17 placed on, and conveyed along, a belt 13 of a conveyor 19, one sample vessel holder 1 and one sample vessel 17 one by one to the downstream side of either the conveyor 19 or a sub-conveyor 119 as necessary.

Figure 15:
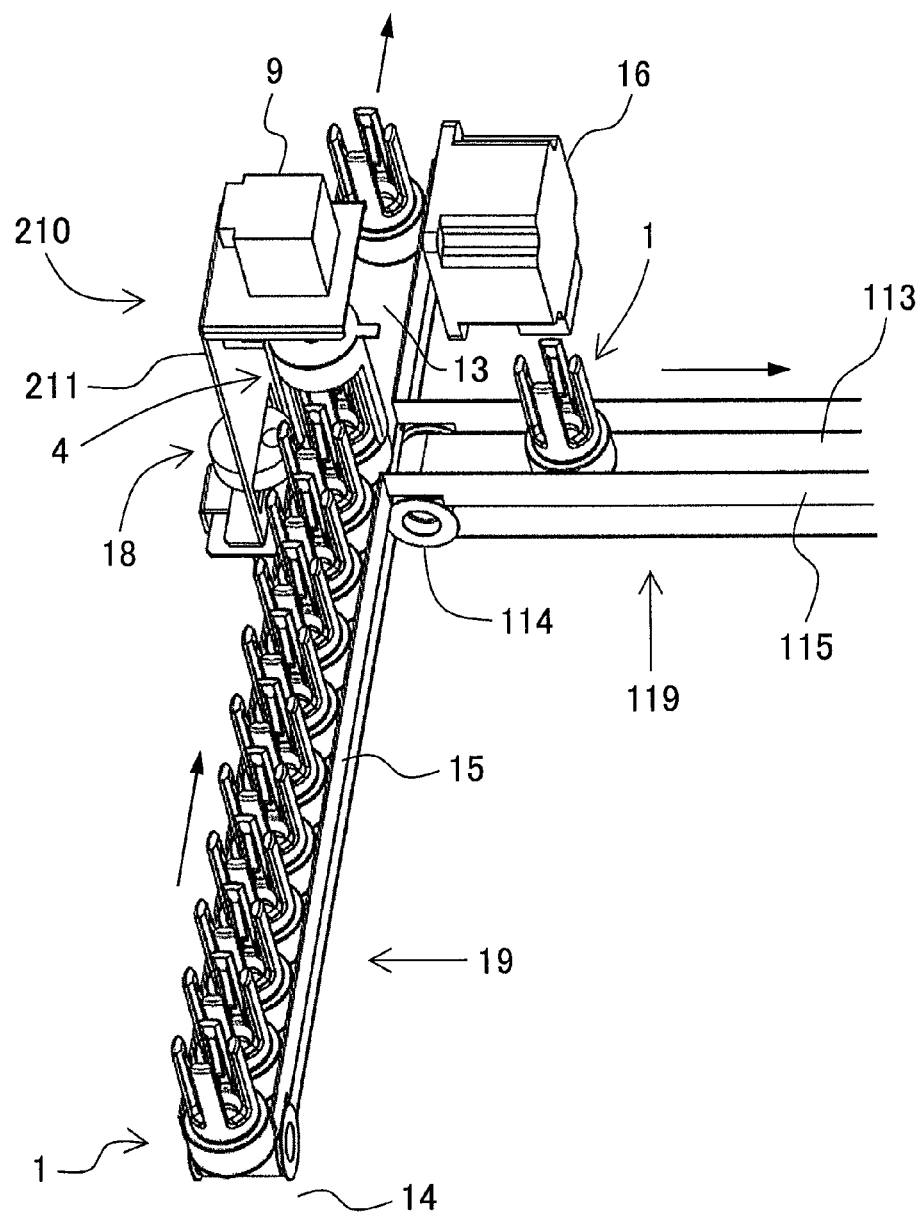
FIG. 15 is a perspective view schematically showing a representative configuration of a conveying unit according to a third embodiment of the present invention, which conveys the sample vessel holders only.

FIG. 15 is a perspective view schematically showing a representative configuration of a conveying unit according to this embodiment conveying the sample vessel holders only. Like or corresponding parts are identified by the same reference numerals as those used in the first embodiment and descriptions for those parts will not be duplicated.

In FIG. 15, the conveying unit of this embodiment generally includes the conveyor 19, the sub-conveyor 119, and a holder holding mechanism 210. Specifically, the conveyor 19 assumes a conveying path for the sample vessel 17 and the sample vessel holder 1 for holding therein the sample vessel 17. The sub-conveyor 119 unloads the sample vessel holder 1 onto the conveyor 19 from a lateral direction of the conveyor 19. The holder holding mechanism 210 is disposed at a portion at which the conveyor 19 merges with the sub-conveyor 119 and controls flow of the sample vessel holders 1. It is noted that, in this embodiment, the left-hand side and the right-hand side in FIG. 15 are the upstream side and the downstream side, respectively, of the sub-conveyor 119.

The conveyor 19 includes pulleys 14, the belt 13, a drive motor 16, and holder guides 15. The pulleys 14 (only one on the upstream side is shown) are rotatably disposed on both upstream (the lower side in FIG. 15) and downstream (the upper side in FIG. 15) ends of a frame not shown. The belt 13 is trained over the pulleys 14 on both ends. The drive motor 16 is coupled to the downstream pulley. The holder guides 15 disposed on both sides of the belt 13 prevent the sample vessel holder 1 conveyed on the belt 13 from being laterally deviated. Driving the downstream pulley with the drive motor 16 causes the belt 13 to be circulatingly driven between the upstream and downstream pulleys 14, resulting in the sample vessel holder 1 placed on the belt 13 being conveyed to the downstream side along the holder guides 15. It is noted that a case in which an upper surface of the belt 13 moves toward the downstream side is forward drive, while a case in which the upper surface of the belt 13 moves toward the upstream side is reverse drive.

The sub-conveyor 119 includes pulleys 114, a belt 113, a drive motor (not shown), and holder guides 115. The pulleys 114 (only one on the upstream side is shown) are rotatably disposed on both upstream (the left-hand side in FIG. 15) and downstream (the right-hand side in FIG. 15) ends of a frame not shown. The belt 113 is trained over the pulleys 114 on both ends. The drive motor is coupled to the downstream pulley. The holder guides 115 disposed on both sides of the belt 113 prevent the sample vessel holder 1 conveyed on the belt 113 from being laterally deviated. The sub-conveyor 119 has an upstream end portion disposed so as to be opposed to and close to a lateral side (a portion partially removed from the holder guide 15) of the conveyor 19. Driving the downstream pulley with the drive motor causes the belt 113 to be circulatingly driven between the upstream and downstream pulleys 114, resulting in the sample vessel holder 1 placed on the belt 113 being conveyed to the downstream side, specifically, the side opposite to the conveyor 19 along the holder guides 115. It is noted that a case in which an upper surface of the belt 113 moves toward the downstream side is forward drive, while a case in which the upper surface of the belt 113 moves toward the upstream side is reverse drive.

The holder holding mechanism 210 is disposed at a portion at which the sub-conveyor 119 branches from the conveyor 19. The holder holding mechanism 210 includes a base 211, a holder holding section 4, a drive motor 9, and a pusher mechanism 18. The holder holding section 4 is disposed at a portion of the conveyor 19 as the conveying path from which the sub-conveyor 119 branches. The drive motor 9 rotatably drives the holder holding section 4 in the horizontal direction. The pusher mechanism 18 pushes the sample vessel holder 1 held in the holder holding section 4 to the side of the sub-conveyor 119.

The pusher mechanism 18 is disposed on a side of the conveyor 19 and on an opposite side of the sub-conveyor 119 across the holder holding section 4. The pusher mechanism 18 has a disk shape having a vertically extending rotational shaft provided eccentrically. In addition, the pusher mechanism 18 is formed to have a thickness thinner than that of a base section 2 of the sample vessel holder 1. The rotational shaft is rotatably driven by a drive motor not shown. This causes the pusher mechanism 18 to protrude onto the conveyor 19 from a lateral side of the conveyor 19 and abut against a lateral side of the base section 2 of the sample vessel holder 1 from between the holder holding section 4 and the belt 13, thereby pushing the sample vessel holder 1 onto the side of the sub-conveyor 119.

Other arrangements are the same as those of the first embodiment of the present invention.

Basic operations of the conveying unit of this embodiment will be described below.

To unload the sample vessel holder 1 placed on the upstream side of the holder holding mechanism 210 in the conveyor 19 to the downstream side of the conveyor 19, the conveying unit first sets up a condition in which an opening 6a in the holder holding section 4 in the holder holding mechanism 210 faces toward the upstream side of the conveyor 19 (specifically, a condition in which a sensor 12 detects a direction detecting protrusion 8b). Under this condition, the belt 13 of the conveyor 19 and the belt 113 of the sub-conveyor 119 are circulatingly driven in the forward direction to thereby place the sample vessel holder 1 on the upstream side of the holder holding mechanism 210 in the conveyor 19. This causes the belt 13 to convey the sample vessel holder 1 toward the downstream side.

At this time, the sample vessel holder 1 placed on the conveyor 19 is loaded into an inside of the holder holding section 4 through the opening 6a in the holder holding section 4 (loaded condition). A sample vessel holding section 3 of the sample vessel holder 1 then contacts an inner periphery of a holding plate 6 on the downstream side of the holder holding section 4. This brings the sample vessel holder 1 to a stop as a result of the sample vessel holder 1 resisting to a friction force acting on the base section 2 thereof from the belt 13. When a plurality of sample vessel holders 1 is then placed on the upstream side of the holder holding mechanism 210, the base section 2 of each of the sample vessel holders 1 contacts the base section of a corresponding sample vessel holder 1 on the downstream side, so that the sample vessel holder 1 is stopped as a result of its resisting to the friction force from the belt 13.

Next, the holder holding section 4 is rotated about a shaft 7 by the drive motor 9 in a clockwise direction as viewed from above, specifically, such that the opening 6a faces in a direction opposite to the sub-conveyor 119. The holding plate 6 is disposed so as to exist at least at an opposite position of an outer peripheral portion of a columnar space C. Thus, while the sample vessel holding section 3 of the sample vessel holder 1 maintains a condition in which it is in contact with the inner periphery of the holding plate 6 of the holder holding section 4, one circumferential end of the holding plate 6 moves past a gap B formed between the sample vessel holder 1 inside the holder holding section 4 and the sample vessel holder 1 adjacent thereto on the upstream side.

When the opening 6a in the holder holding section 4 in the holder holding mechanism 210 then faces toward the downstream side of the conveyor 19 (specifically, when a condition is set up in which the sensor 12 detects a direction detecting protrusion 8a), the sample vessel holder 1 is conveyed toward the downstream side by the belt 13 and unloaded via the opening 6a in the holder holding section 4 out of the holder holding section 4 (unloaded condition). At this time, the sample vessel holder 1 on the upstream side of the holder holding section 4 is brought to a stop as a result of the sample vessel holder 1 resisting to the friction force acting on the base section 2 thereof from the belt 13 because of the sample vessel holding section 3 contacting an outer periphery on the upstream side of the holder holding section 4. The sample vessel holders 1 placed on the upstream side of the holder holding mechanism 210 are stopped as a result of their resisting to the friction force from the belt 13 when the base section 2 of each of the sample vessel holders 1 contacts the base section of a corresponding sample vessel holder 1 on the downstream side.

To further unload the sample vessel holder 1 onto the downstream side of the conveyor 19 from this condition (the condition in which the opening 6a faces toward the downstream side in the conveyor 19), the holder holding section 4 is rotated about the shaft 7 by the drive motor 9 in a counterclockwise direction as viewed from above, specifically, such that the opening 6a faces in the direction opposite to the sub-conveyor 119, to thereby cause the opening 6a in the holder holding section 4 in the holder holding mechanism 210 to face toward the upstream side of the conveyor 19 (specifically, a condition is set up in which the sensor 12 detects the direction detecting protrusion 8b). This allows the sample vessel holder 1 to be conveyed toward the downstream side by the belt 13, so that the sample vessel holder 1 is loaded into the inside of the holder holding section 4 through the opening 6a in the holder holding section 4 (loaded condition).

Alternatively, to unload the sample vessel holder 1 placed on the upstream side of the holder holding mechanism 210 in the conveyor 19 onto the downstream side of the sub-conveyor 119, the conveying unit first sets up a condition in which the opening 6a in the holder holding section 4 in the holder holding mechanism 210 faces toward the upstream side of the conveyor 19 (specifically, a condition in which the sensor 12 detects the direction detecting protrusion 8b). Under this condition, the belt 13 of the conveyor 19 and the belt 113 of the sub-conveyor 119 are circulatingly driven in the forward direction to thereby place the sample vessel holder 1 on the upstream side of the holder holding mechanism 210 in the conveyor 19. This causes the belt 13 to convey the sample vessel holder 1 toward the downstream side.

At this time, the sample vessel holder 1 placed on the sub-conveyor 119 is loaded into the inside of the holder holding section 4 through the opening 6a in the holder holding section 4 (loaded condition). The sample vessel holding section 3 of the sample vessel holder 1 then contacts the inner periphery on the downstream side, in the conveyor 19, of the holding plate 6 of the holder holding section 4. This brings the sample vessel holder 1 to a stop as a result of the sample vessel holder 1 resisting to the friction force acting on the base section 2 thereof from the belt 13. When a plurality of sample vessel holders 1 is then placed on the upstream side of the holder holding mechanism 210 in the sub-conveyor 119, the base section 2 of each of the sample vessel holders 1 contacts the base section of a corresponding sample vessel holder 1 on the downstream side, so that the sample vessel holder 1 is stopped as a result of its resisting to the friction force from the belt 113. The sample vessel holders 1 placed on the conveyor 19 are stopped as a result of their resisting to the friction force from the belt 13 when the base section 2 of the sample vessel holder 1 loaded in the inside of the holder holding section 4 contacts the base section of the sample vessel holder 1 on the downstream side.

Next, the holder holding section 4 is rotated about the shaft 7 by the drive motor 9 in the counterclockwise direction as viewed from above, specifically, such that the opening 6a faces toward the downstream side of the conveyor 19. The holding plate 6 is disposed so as to exist at least at an opposite position of the outer peripheral portion of the columnar space C. Thus, while the sample vessel holding section 3 of the sample vessel holder 1 maintains a condition in which it is in contact with the inner periphery of the holding plate 6 of the holder holding section 4, one circumferential end of the holding plate 6 moves past the gap B formed between the sample vessel holder 1 inside the holder holding section 4 and the sample vessel holder 1 adjacent thereto on the upstream side in the sub-conveyor 119.

Then, a condition is set up in which the opening 6a in the holder holding section 4 in the holder holding mechanism 210 faces toward the side of the sub-conveyor 119 (specifically, a condition is set up in which the holder holding section 4 is rotated 90° in the counterclockwise direction as viewed from above from the condition in which the sensor 12 detects the direction detecting protrusion 8b). The pusher mechanism 18 is then rotatably driven to push the sample vessel holder 1 onto the side of the sub-conveyor 119. As a result, the sample vessel holder 1 is pushed onto the sub-conveyor 119 and conveyed toward the downstream side by the belt 113 (unloaded condition). At this time, the sample vessel holder 1 on the upstream side of the holder holding section 4 in the conveyor 19 is brought to a stop as a result of the sample vessel holder 1 resisting to the friction force acting on the base section 2 thereof from the belt 13 because of the sample vessel holding section 3 contacting the outer periphery on the upstream side of the holder holding section 4. The sample vessel holders 1 placed on the upstream side of the holder holding mechanism 210 in the conveyor 19 are stopped as a result of their resisting to the friction force from the belt 13 when the base section 2 of each of the sample vessel holders 1 contacts the base section of a corresponding sample vessel holder 1 on the downstream side.

To unload the sample vessel holder 1 additionally onto the downstream side of the sub-conveyor 119 from this condition (the condition in which the opening 6a faces toward the downstream side in the conveyor 19), the holder holding section 4 is rotated about the shaft 7 by the drive motor 9 in the clockwise direction as viewed from above, to thereby cause the opening 6a in the holder holding section 4 in the holder holding mechanism 210 to face toward the upstream side of the conveyor 19 (specifically, a condition is set up in which the sensor 12 detects the direction detecting protrusion 8b). This allows the sample vessel holder 1 to be conveyed toward the downstream side by the belt 13, so that the sample vessel holder 1 is loaded into the inside of the holder holding section 4 through the opening 6a in the holder holding section 4 (loaded condition).

Other operations are the same as those in the first embodiment.

The same effects as those achieved in the first embodiment can also be achieved in this embodiment having the arrangements as described above.

Fourth Embodiment

A fourth embodiment of the present invention will be described below with reference to the accompanying drawings.

This embodiment is configured so as to control the flow of sample vessel holders 1 by unloading every predetermined plurality of sample vessel holders 1 and sample vessels 17 (three each in this embodiment) as necessary out of a plurality of sample vessel holders 1 and sample vessels 17 placed on, and conveyed from the upstream side along, a belt 13 of a conveyor 19.

FIG. 16 is a perspective view schematically showing a representative configuration of a conveying unit according to this embodiment conveying the sample vessel holders only. FIG. 17 is a top view including a partial cross-sectional view. Like or corresponding parts are identified by the same reference numerals as those used in the first embodiment and descriptions for those parts will not be duplicated.

In FIG. 16, the conveying unit of this embodiment generally includes the conveyor 19 and a holder holding mechanism 310. Specifically, the conveyor 19 assumes a conveying path for the sample vessel holder 1 for holding therein the sample vessel 17. The holder holding mechanism 310 controls flow of the sample vessel holders 1 on the conveyor 19. It is noted that, in the following, the upper side and the lower side in FIG. 16 will be referred to as the downstream side and the upstream side, respectively, of the conveying unit.

The holder holding mechanism 310 includes a base 11, a holder holding section 304 disposed on the conveyor 19 as the conveying path, and a drive motor 9 that rotatably drives the holder holding section 304 in the horizontal direction.

The holder holding section 304 includes a shaft 7, a holding plate base 305, and two holding plates 306a, 306b. Specifically, the shaft 7 having a central axis extending in the vertical direction is rotatably disposed on the base 11. The holding plate base 305 is disposed at a lower end of the shaft 7. The holding plates 306a, 306b are disposed on the holding plate base 305 so as to extend along an outer peripheral portion of a columnar space D centered about the central axis of the shaft 7. Rotatably driving the shaft 7 with the drive motor 9 causes the holding plates 306a, 306b to move in a circumferential direction along the outer peripheral portion of the columnar space D. The drive motor 9 is, for example, a stepping (pulse) motor having a rotational angle controlled based on a control signal from a general control unit 30.

The two holding plates 306a, 306b of the holder holding section 304 will be described in detail below. As shown in FIG. 17, the holding plates 306a, 306b each have a partially columnar shape disposed along the outer peripheral portion of the columnar space D. The holding plates 306a, 306b are disposed at diametrically opposite positions across the shaft 7. Precisely, the holding plates 306a, 306b are disposed such that one of pairs of end portions thereof at the diametrically opposite positions is symmetrical relative to a central axis of the columnar space D. This results in the following when the holder holding section 304 is rotatably driven about the shaft 7 (specifically, the holding plates 306a, 306b are moved circumferentially). Specifically, when either one of the holding plates 306a, 306b is disposed on the conveyor 19, the other one of the holding plates 306a, 306b is disposed outside the conveyor 19; and either one of the holding plates 306a, 306b moves to advance into (or retract from) the conveyor 19, the other one of the holding plates 306a, 306b moves to retract from (or advance into) the conveyor 19. It is noted that, of the two holding plates 306a, 306b, the one disposed on the upstream side in the conveyor 19 is denoted 306a and the one disposed on the downstream side of the conveyor 19 is denoted 306b.

A plate 308 is fixed relative to the holding plate base 305 at a position above the holding plate base 305. The plate 308 has a direction detecting protrusion (not shown) protruding outwardly in a radial direction. In addition, a sensor 12 is fixed to the base 11 at a position past which the direction detecting protrusion moves as the holder holding section 304 rotates circumferentially. The direction detecting protrusion of the plate 308 is disposed so as to move past and be detected by the sensor 12 when either one of the holding plates 306a, 306b is positioned on the conveyor 19. A detection signal of the sensor 12 is sent to the general control unit 30.

The holding plate base 305 of the holder holding section 304 is disposed at a level higher than a height of an upper end of the sample vessel holder 1 placed on the conveying path, from a conveying surface of the conveyor 19.

The holder holding section 304 is formed to have an inside diameter, the inside diameter being, specifically, an inside diameter of a cylindrical space through which the holding plates 306a, 306b pass as the holder holding section 304 rotates about the shaft 7 (an outer periphery of the columnar space D), such that the multiple (three in this embodiment) sample vessel holders 1 disposed adjacent to each other on the conveyor 19 can be contained at once. An outside diameter of the holding plate 306, or to state the foregoing differently, an outside diameter of the cylindrical space through which the holding plates 306a, 306b pass as the holder holding section 304 rotates about the shaft 7 is formed such that an outer periphery of a sample vessel holding section 3 of a first sample vessel holder 1 does not contact the sample vessel holding section 3 of a second sample vessel holder 1 adjacent to the first sample vessel holder 1 when, out of the multiple (three in this embodiment) sample vessel holders 1 disposed adjacent to each other, the one on the downstream side is inscribed in the holding plate 306b. Thus, if the holder holding section 304 is rotated about the shaft 7 in the counterclockwise direction under this condition (the condition shown in, for example, FIGS. 16 and 17), the holding plate 306a moves through a gap B formed between the adjacent sample vessel holders 1.

Other arrangements are the same as those in the first embodiment of the present invention.

Basic operations of the conveying unit of this embodiment will be described below.

To unload three each of multiple sample vessel holders 1 placed on the conveyor 19 to the downstream side, the conveying unit first sets up a condition in which the holding plate 306b on the downstream side of the holder holding section 304 in the holder holding mechanism 310 is positioned on the conveyor 19 (specifically, the sensor 12 detects the direction detecting protrusion). Under this condition, the belt 13 of the conveyor 19 is circulatingly driven in the forward direction to thereby place a plurality of sample vessel holders 1 on the upstream side of the holder holding mechanism 310. This causes the belt 13 to convey the sample vessel holders 1 toward the downstream side.

At this time, the sample vessel holding section 3 of the sample vessel holder 1 positioned on the conveyor 19 contacts the inner peripheral side of the holding plate 306b. This brings the sample vessel holders 1 to a stop as a result of the sample vessel holders 1 resisting to a friction force acting on base sections 2 thereof from the belt 13 (loaded condition). Additionally, the base section 2 of each of the sample vessel holders 1 contacts the base section of a corresponding sample vessel holder 1 on the downstream side, so that the sample vessel holder 1 is stopped as a result of its resisting to the friction force from the belt 13.

The holder holding section 304 is then rotated about the shaft 7 by the drive motor 9 in the counterclockwise direction as viewed from above. At this time, while the sample vessel holding section 3 of the sample vessel holder 1 on the most downstream side maintains a condition in which it is in contact with the inner periphery of the holding plate 306b on the downstream side of the holder holding section 304, the holding plate 306a on the upstream side advances into the gap B formed between the sample vessel holder 1 in the third position on the upstream side from the sample vessel holder 1 on the most downstream side and the sample vessel holder 1 adjacent thereto on the upstream side.

When a condition is then set up in which the holding plate 306a of the holder holding section 304 in the holder holding mechanism 310 is positioned on the conveyor 19 (specifically, the sensor 12 detects the direction detecting protrusion), three sample vessel holders 1 are conveyed toward the downstream side by the belt 13 (unloaded condition). At this time, the sample vessel holder 1 on the upstream side of the holder holding section 304 is brought to a stop as a result of the sample vessel holder 1 resisting to the friction force acting on the base section 2 thereof from the belt 13 because of the sample vessel holding section 3 contacting the holding plate 306a on the upstream side of the holder holding section 304.

When the holding plate 306b of the holder holding section 304 on the downstream side in the holder holding mechanism 310 is positioned on the conveyor 19 (specifically, the sensor 12 detects the direction detecting protrusion), the sample vessel holder 1 is conveyed toward the downstream side by the belt 13 and the sample vessel holding section 3 contacts the inner peripheral side of the holding plate 306b, so that the sample vessel holder 1 is stopped as a result of its resisting to the friction force from the belt 13 acting on the base section 2 (loaded condition).

As described above, the conveying unit of this embodiment unloads every predetermined plurality of sample vessel holders 1 as necessary out of a plurality of sample vessel holders 1 placed on the belt 13 of the conveyor 19 onto the downstream side, thereby controlling the flow of the sample vessel holders 1.

Other operations are the same as those in the first embodiment.

The same effects as those achieved in the first embodiment can also be achieved in this embodiment having the arrangements as described above.

DESCRIPTION OF REFERENCE NUMERALS

1: Sample vessel holder
2: Base section
3: Sample vessel holding section
4, 4A, 304: Holder holding section
5, 305: Holding plate base
6, 306a, 306b: Holding plate
7: Shaft
8, 308: Plate
9: Drive motor
10, 10A, 210, 310: Holder holding mechanism
11, 11A, 211: Base
12: Sensor
13, 113: Belt
14, 114: Pulley
15, 115: Holder guide
16: Drive motor
17: Sample vessel
18: Pusher mechanism
19: Conveyor
30: General control unit
31: Plugging module
32: Classifying module
33: Storing module
34: Loading module
35: Centrifuging module
36: Unplugging module
37: Labeler
38: Dispensing module
39: Automatic analyzer
40: Conveying unit

The invention claimed is:
1. A sample processing system comprising:
a plurality of sample vessel holders each including a disk-shaped base section having a central axis extending in a vertical direction, and a sample vessel holding section that is disposed coaxially with, and above, the base section and has an outside diameter less than that of the base section, each sample vessel holding section is configured to hold a sample vessel in an upright posture;

a conveying path that conveys the plurality of sample vessel holders placed thereon in a transport direction along the conveying path; and a holder holding mechanism, disposed adjacent to the conveying path, including a holding plate disposed extending along an outer peripheral portion of a columnar space that has a central axis extending in the vertical direction, wherein the holding plate has an open portion through which a sample vessel holder on the conveying path passes into the columnar space, wherein a drive motor is configured to rotate the holding plate around the central axis of the columnar space thereby rotating the open portion, wherein at least a portion of the holding plate rotates in a gap between the sample vessel holder holding the sample vessel in the columnar space and an adjacent sample vessel holder on the conveying path, and wherein the holder holding mechanism blocks or permits the sample vessel holder from being conveyed on the conveying path downstream of the holder holding mechanism in the transport direction based on an orientation of the open portion of the holding plate, which is rotated by the drive motor.

2. The sample processing system according to claim 1, wherein the transportation direction is switched by a circumferential movement of the holding plate, driven by the drive motor, between a loading state in which the sample vessel holder is loaded into an inside of the columnar space and an unloading state that permits unloading of the sample vessel holder inside the columnar space onto the conveyance path to be conveyed downstream of the holder holding mechanism while preventing loading of other sample vessel holder into the columnar space.

3. The sample processing system according to claim 2, wherein the columnar space defined by the holding plate has an inside diameter that is substantially an integral multiple of an outside diameter of the base section of the sample vessel holder.

4. The sample processing system according to claim 3, further comprising:

direction detecting means for detecting a circumferential position at which the holding plate exists; and control means for controlling the rotational driving means based on a result of detection supplied from the direction detecting means.

5. The sample processing system according to claim 2, further comprising:

direction detecting means for detecting a circumferential position at which the holding plate exists; and control means for controlling the rotational driving means based on a result of detection supplied from the direction detecting means.

6. The sample processing system according to claim 1, further comprising:

direction detecting means for detecting a circumferential position at which the holding plate exists; and control means for controlling the rotational driving means based on a result of detection supplied from the direction detecting means.

7. The sample processing system according to claim 1, wherein the columnar space defined by the holding plate has an inside diameter that is substantially an integral multiple of an outside diameter of the base section of the sample vessel holder.

8. The sample processing system according to claim 1, wherein the conveying path is a first conveying path and the transport direction is a first transport direction, wherein the sample processing system further comprises a second conveying path configured to convey one or more of the plurality of the sample vessel holders in a second transport direction, which is different than the first transport direction, along the second conveying path, wherein the first conveying path and the second conveying path intersect with each other, and wherein the drive motor rotates the holding plate such that the open portion of the holding plate opens toward the second conveying path.

* * * * *